United States Patent [19]

Rahmim et al.

[11] Patent Number: 5,157,194
[45] Date of Patent: Oct. 20, 1992

[54] HIGHLY SELECTIVE N-OLEFIN ISOMERIZATION PROCESS USING MICROCRYSTALLINE ZSM-22

[75] Inventors: Iraj Rahmim, Turnersville, N.J.; Albin Huss, Jr., Chadds Ford; Daria N. Lissy, Glen Mills, both of Pa.; Donald J. Klocke, Somerdale; Ivy D. Johnson, Medford, both of N.J.

[73] Assignee: Mobil Oil Corporation, Fairfax, Va.

[21] Appl. No.: 811,355

[22] Filed: Dec. 20, 1991

[51] Int. Cl.$^5$ ................................. C07C 5/22
[52] U.S. Cl. ................................. 585/671
[58] Field of Search ........................ 585/671

[56] References Cited

U.S. PATENT DOCUMENTS 4,912,073  3/1990  Chu ........................... 502/85
4,922,048  5/1990  Harandi ..................... 585/310

FOREIGN PATENT DOCUMENTS 0026041  4/1981  European Pat. Off. .
0247802  12/1987  European Pat. Off. .

Primary Examiner—Patrick P. Garvin
Assistant Examiner—E. D. Irzinski
Attorney, Agent, or Firm—Alexander J. McKillop; Charles J. Speciale; Laurence P. Hobbes

[57] ABSTRACT

A process is disclosed for the highly selective skeletal isomerization of linear olefin-containing organic feeds to iso-olefins at high levels of feed conversion wherein linear olefins, e.g., n-butenes, are contacted with catalyst comprising ZSM-22 having a crystal size whose largest dimension is no greater than 0.5 micron. The process is carried out under isomerization conditions to produce iso-olefins of corresponding carbon number, e.g., isobutene. High overall iso-olefin yields thus can be obtained, even at relatively low temperatures.

18 Claims, 2 Drawing Sheets

HIGHLY SELECTIVE N-OLEFIN ISOMERIZATION PROCESS USING MICROCRYSTALLINE ZSM-22

FIELD OF THE INVENTION

This invention relates to a method for the high level conversion of n-olefin-containing, e.g. n-butene-containing, hydrocarbon streams to iso-olefin-rich, e.g., isobutene-rich product streams. The process uses a catalyst composition comprising microcrystalline ZSM-22, i.e., ZSM-22 having a crystal size whose largest dimension is no greater than 0.5 microns and whose ratio of its second largest dimension to said largest dimension ranges from 0.5 to 1.

BACKGROUND OF THE INVENTION

The demand for iso-alkenes has recently increased. For example, relatively large amounts of isobutene are required for reaction with methanol or ethanol over an acidic catalyst to produce methyl tert-butyl ether (MTBE) or ethyl tert-butyl ether (ETBE) which is useful as an octane enhancer for unleaded gasolines. Isoamylenes are required for reaction with methanol over an acidic catalyst to produce tert-amyl methyl ether (TAME). With passage of the Clean Air Act in the United States mandating increased gasoline oxygenate content, MTBE, ETBE and TAME have taken on new value as clean-air additives, even for lower octane gasolines. Lead phasedown of gasolines in Western Europe has further increased the demand for such oxygenates.

An article by J. D. Chase, et al., *Oil and Gas Journal*, Apr. 9, 1979, discusses the advantages one can achieve by using such materials to enhance gasoline octane. The blending octane values of MTBE when added to a typical unleaded gasoline base fuel are RON=118, MON=101, R+M/2=109. The blending octane values of TAME when added to a typical unleaded gasoline base fuel are RON=112, MON=99, R+M/2=106. Isobutene (or isobutylene) is in particularly high demand as it is reacted with methanol to produce MTBE.

The addition of shape-selective zeolite additives such as ZSM-5 to cracking catalysts, e.g. those used in fluidized catalytic cracking (FCC), is beneficial in producing gasoline boiling range product of increased octane rating. However, increased amounts of olefins result, including n-butenes, creating a need for their conversion to higher value products such as isobutene which can be used to produce MTBE.

Butene exists in four isomers: butene-1, cis-butene-2, its stereo-isomer trans-butene-2, and isobutene. Conversions between the butenes-2 is known as geometric isomerization, whereas that between butene-1 and the butenes-2 is known as position isomerization, double-bond migration, or hydrogen-shift isomerization. The aforementioned three isomers are not branched and are known collectively as normal or n-butenes. Conversion of the n-butenes to isobutene, which is a branched isomer, is widely known as skeletal isomerization.

The reaction of tertiary olefins with alkanol to produce alkyl tertiary alkyl ether is selective with respect to iso-olefins. Linear olefins are unreactive in the acid catalyzed reaction, even to the extent that it is known that the process can be utilized as a method to separate linear and iso-olefins. The typical feedstream of FCC $C_4$ or $C_4+$ crackate used to produce tertiary alkyl ethers in the prior art which contains normal butene and isobutene utilizes only the branched olefin in etherification. This situation presents an exigent challenge to workers in the field to discover a technically and economically practical means to utilize linear olefins, particularly normal butene, in the manufacture of tertiary alkyl ethers.

In recent years, a major development within the petroleum industry has been the discovery of the special catalytic capabilities of a family of zeolite catalysts based upon medium pore size shape selective metallosilicates. Discoveries have been made leading to a series of analogous processes drawn from the catalytic capability of zeolites in the restructuring of olefins.

European Pat. No. 0026041 to Garwood, incorporated herein by reference, discloses a process for the restructuring of olefins in contact with zeolite catalyst to produce iso-olefins, followed by the conversion of iso-olefins to MTBE and TAME. The restructuring conditions comprise temperature between 204° C. and 315° C. and pressure below 51 kPa.

U.S. Pat. No. 4,922,048 to Harandi discloses the use of a wide variety of medium pore size zeolites, e.g. ZSM-5, ZSM-11, ZSM-12, ZSM-22, ZSM-23, ZSM-35 and ZSM-48, in low temperature (232°-385° C.) olefin interconversion of $C_2$-$C_6$ olefins to products including tertiary $C_4$-$C_5$ olefins and olefinic gasoline.

In European Pat. No. 0247802 to Barri et al, it is taught that linear olefins can be restructured in contact with zeolite catalyst, including Theta-1 (ZSM-22) and ZSM-23, to produce branched olefins. The restructuring conditions comprise temperature between 200°-550° C., pressure between 100 and 5000 kPa and WHSV between 1 and 100. Selectivities to isobutene up to 91.2% are reported using a calcined Theta-1 tectometallosilicate at 400° C. and 30.6% 1-butene conversion. All of the above references are incorporated herein by reference.

Despite the efforts exemplified in the above references, the skeletal isomerization of olefins e.g., to produce isobutene, has been hampered by relatively low conversion and/or selectivity to isobutene perhaps owing to the lability of these olefins. It is further known that skeletal isomerization becomes more difficult as hydrocarbons of lower molecular weight are used, requiring more severe operating conditions, e.g. higher temperatures and lower linear olefin partial pressures.

Generally, the conversion of n-butenes to iso-butene is conducted at selectivities below 90%. In order to obtain higher selectivities, operation at high temperatures (>500° C.) and with high feed dilution (butene partial pressure, typically less than 5 psia (34.5 kPa)) is generally required. Selectivities of greater than 85%, 90%, 95% or even 99% are highly advantageous in commercial conversion of n-butenes to isobutene in order to avoid the need to separate out materials other than n-butene from the product stream. Such high selectivities will permit direct (cascading) or indirect introduction of the isomerizer effluent to an etherification zone where isobutene is reacted with alkanol to produce alkyl tert-butyl ether, e.g. MTBE. Unconverted n-butenes in the isomerizer effluent can be withdrawn either before the etherification zone or preferably, from the etherification zone effluent insofar as the etherification reaction utilizes only the isobutene component of the isomerizer stream. Unreacted n-butenes from the etherification zone effluent can be recycled to the isomerizer where they are converted to isobutene at high selectivity. If the recycle stream contains not only unconverted linear olefins, e.g. n-butenes, but also by-products such as other olefins (e.g. propylene) or paraffins, they have to be removed from the recycle stream, such as by distillation or by taking a slip stream. These removal steps are expensive and can lead to considerable loss of not only the by-products but butenes as well. These losses are larger when the by-products formed are present in higher concentration. Thus, even small improvements in the isobutene selectivity during n-butene isomerization have a major effect on the commercial viability of the process. However, high selectivities in skeletal isomerization processes have generally required low linear olefin partial pressures and high temperatures which place substantial limitations on such processes. It would, therefore, be advantageous to provide a skeletal isomerization catalyst capable of maintaining relatively high selectivity at low temperatures and high linear olefin partial pressures.

Further enhancement of total yield of iso-olefin can be effected by enhancing overall conversion of the n-olefin-containing feedstream. With this object in mind, it would be advantageous to provide a skeletal isomerization catalyst capable of maintaining a high level of conversion as well as high iso-olefin selectivity, even at relatively low temperatures, e.g., no greater than 450° C. and high n-olefin space velocities, e.g., no less than 5, e.g., no less than 70.

SUMMARY OF THE INVENTION

The present invention provides a method for conversion of linear olefins to corresponding iso-olefins of the same carbon number which comprises contacting a linear olefin-containing organic feedstock with a catalyst comprising microcrystalline ZSM-22, under skeletal isomerization conditions. Microcrystalline ZSM-22 can be described as having a crystal morphology whose largest dimension is no greater than 0.5 micron, and whose ratio of its second largest dimension to said largest dimension ranges from about 0.5 to 1.

In one aspect, the present invention can provide enhanced overall yields of iso-olefin product from linear olefin-containing feeds by a highly selective conversion of linear olefins to corresponding iso-olefins of the same carbon number, e.g. n-butenes to isobutene, at enhanced linear olefin conversion levels.

The advantage of the present invention arises from the capacity of the catalyst employed to operate at conversion levels which are relatively high, while maintaining excellent isobutene selectivity. Although European Pat. No. 0247802 to Barri et al, teaches that linear olefins can be restructured by contacting with zeolite catalyst, including Theta-1, an isotype of ZSM-22, to produce branched olefins in a highly selective reaction, the catalytic material exemplified therein comprises large crystal Theta-1 which is a relatively low activity catalyst, particularly at lower temperatures, e.g. 400° C. The Theta-1 crystals have acicular lathe (needle-like) morphology with a broad distribution of crystal sizes having the largest dimension of up to 1 to 2 microns.

The present invention's utilization of microcrystalline ZSM-22 results in not only a highly selective conversion of n-olefins to iso-olefins, but a conversion of n-olefin feed at significantly higher levels, over a broad temperature range, particularly at temperatures of less than about 500° C., 450° C. or even 400° C.

The high selectivity of ZSM-22 in the present invention results in large part from isomerization occurring without significant conversion to lighter and heavier molecules. This phenomenon, it is believed, is a consequence of the pore structure of ZSM-22 which promotes isomerization at a much faster rate than the reaction by which say, butene, is converted to lighter (mostly propylene) and heavier olefins (olefin interconversion reaction). Moreover, such isomerization takes place without significant cracking of the feed or hydrogenation or dehydrogenation effects resulting in the formation of, say, n-butane or butadiene. The present invention can be used to effect conversion of linear olefins to iso-olefins while resulting in less than 30%, 10%, 5% or even less than 1% by weight of converted product having lower or higher average carbon number, while operating at high linear olefin conversion levels, e.g. no less than 25, 35, or 45%, or even higher.

DETAILED DESCRIPTION OF THE INVENTION

Figure 1:
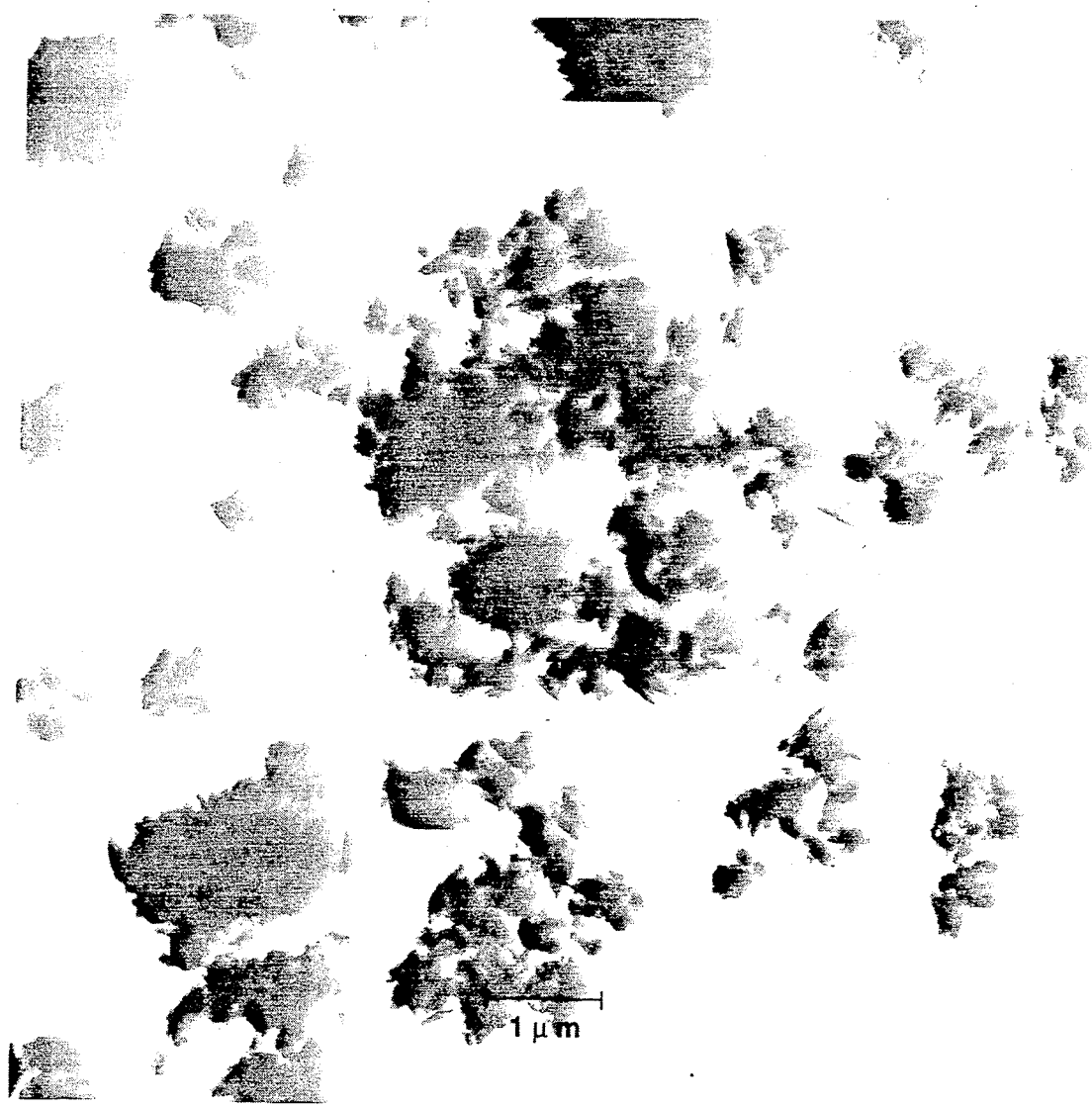
FIG. 1 is a transmission electron microscopy (TEM) micrograph of a microcrystalline ZSM-22 sample prepared in accordance with the procedure set out in Example 1.

The present invention provides a process which converts a linear olefin-containing hydrocarbon feedstream to an iso-olefin rich product at high levels of conversion and high iso-olefin selectivity over a catalyst comprising material having the structure of ZSM-22 and having a crystal size whose largest dimension is no greater than 0.5 micron, preferably no greater than 0.3 micron, under skeletal isomerization conditions. Such conditions comprise temperatures between about 250° and 750° C., weight hourly space velocities (WHSV) based on linear olefins in said feedstock between 1 and 500 WHSV, linear olefin partial pressures between 12 and 500 kPa, and conversion levels of linear olefins at least 20 weight percent.

For present purposes, "ZSM-22" is considered equivalent to its isotypes, which include Theta-1 (S. A. I. Barri, G. W. Smith, D. White and D. Young, Nature 312, 533 (1984), R. M. Highcock, G. W. Smith and D. Wood, Acta Cryst. C41, 1391 (1985); ISI-1 (T. Kozo and K. Noboru, European patent application 170,003 (1986)); KZ-2 (L. M. Parker and D. M. Bibby, Zeolites 3, 8 (1983)); and NU-10 (A. Araya and B. M. Lowe, Zeolites 4, 280 (1984)).

The skeletal isomerization reaction of the present invention is carried out at temperatures between 250° and 750° C.; weight hourly space velocity based on linear olefin in the feed between 1 and 500 WHSV; and linear olefin partial pressure between 12 and 500 kPa. The preferred conditions are temperatures between 325° and 600° C., more preferably between 390° and 550° C., WHSV between 5 and 400, more preferably between 10 and 250; and a linear olefin partial pressure between 30 and 300 kPa, more preferably between 50 and 150 kPa. Under these conditions the conversion of linear olefin, e.g., n-butene, can be at least 20%, preferably at least 35% and more preferably at least 45%. The selectivity to iso-olefin, e.g., isobutene, is at least 75%, preferably at least 85%, 90%, or even 95%.

The present invention is especially suited to processes carried out at high linear olefin to iso-olefin selectivity, e.g. at least 60% at relatively low conversion temperatures and high linear olefin partial pressures. Such processes can maintain selectivities of at least 75, 85 or 95% at a conversion temperature less than or equal to 550°, 450°, 400° or even 350° C., and linear olefin partial pressures above 2 psia (14 kPa), e.g. above 5 psia (34 kPa). Such processes can be carried out at an overall conversion of linear olefins of at least 30, 35, 40, or 45 wt % or higher. The present method is particularly effective when operating at lower temperatures, e.g. less than 450° C. and at relatively high WHSV, e.g. no less than 5, 10, or even 60. Under these conditions is observed a significant improvement in catalytic activity as evidenced by enhanced conversion of linear olefins when compared with methods utilizing Theta-1 materials of the prior art.

Preferred feedstreams include $C_4$ or $C_4+$ hydrocarbon feedstreams. Linear olefins suited to use in the present invention may be derived from a fresh feedstream, preferably comprising n-butenes and/or n-pentenes, or from the effluent of an iso-olefin etherification reactor which employs alkanol and $C_4$ or $C_4+$ hydrocarbon feedstock. Typical hydrocarbon feedstock materials for isomerization reactions according to the present invention include olefinic streams, such as cracking process light gas containing butene isomers in mixture with substantial amounts of paraffins including n-butane and isobutane. The $C_4$ components usually contain a major amount of unsaturated compounds, such as 10-40% isobutene, 20-55% linear butenes, and small amounts of butadiene. Also, $C_4+$ heavier olefinic hydrocarbon streams may be used, e.g $C_4$ to $C_{10}$, preferably $C_4$ to $C_6$ olefinic hydrocarbon streams.

ZSM-22 is a zeolite having a one-dimensional channel system made up of 10-member rings, elliptical in nature, with a free diameter of 4.7 by 5.5 angstrom units. ZSM-22 and its preparation in large crystal form using hexanediamine as directing agent is more particularly described in U.S. Pat. No. 4,556,477 to Dwyer, the entire contents of which are incorporated herein by reference. U.S. Pat. No. 4,481,177 to Valyocsik, the entire contents of which are incorporated herein by reference, discloses the preparation of microcrystalline ZSM-22 using ethylpyridinium as directing agent and sources of silicon such as colloidal silica or silica sol. For purposes of the present invention, amorphous precipitated silica may also be used as a source of silicon.

As noted above microcrystalline ZSM-22 has a morphology whose largest dimension is no greater than 0.5 micron, preferably no greater than 0.3 micron or even 0.2. Even more preferably such crystals can be described as falling within the range of 0.2 to 0.4 micron by 0.1 to 0.4 micron by <0.1 micron.

The zeolite catalyst used is preferably at least partly in the hydrogen form, e.g. HZSM-22, but other cations, e.g. rare earth cations, may also be present. When the zeolites are prepared in the presence of organic cations, they may be quite inactive possibly because the intracrystalline free space is occupied by the organic cations from the forming solution. The zeolite may be activated by heating in an inert atmosphere to remove the organic cations e.g. by heating at over 500° C. for 1 hour or more. The hydrogen form can then be obtained by base exchange with ammonium salts followed by calcination e.g. at 500° C. in air. Other cations, e.g. metal cations, can be introduced by conventional base exchange or impregnation techniques.

The ZSM-22 may be incorporated in another material usually referred to as a matrix or binder. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the ZSM-22 employed herein may be composited with a porous matrix material, such as silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

Of all the foregoing materials, silica may be preferred as the matrix material owing to its relative inertness for catalytic cracking reactions which are preferably minimized in the instant isomerization processes. The relative proportions of finely divided ZSM-22, and inorganic oxide gel matrix vary widely with the zeolite content ranging from about 1 to about 90 percent by weight and more usually in the range of about 30 to about 80 percent by weight of the composite.

The regeneration of spent zeolite catalyst used in the isomerization reaction is carried out oxidatively or hydrogenatively employing procedures known in the art. The catalyst of the present invention can be readily reactivated without significantly reducing selectivity for isobutene by exposing it to hydrogen for a suitable period, e.g. overnight.

In order to obtain desired linear olefin skeletal isomerization activity/selectivity, ZSM-22, preferably in the hydrogen form, should have an alpha value of at least 5, preferably at least 50 when used in the catalyst of the present invention. Alpha value, or alpha number, of a zeolite is a measure of zeolite acidic functionality and is more fully described together with details of its measurement in U.S. Pat. No. 4,016,218, *J. Catalysis*, 6, pp. 278-287 (1966) and *J. Catalysis*, 61, pp. 390-396 (1980). The experimental conditions cited in the latter reference are used for characterizing the catalysts described herein.

The examples which follow illustrate the invention without restricting it in any way.

EXAMPLE 1

Preparation of Microcrystalline ZSM-22

Microcrystalline ZSM-22 was prepared by charging the following to a 5 gallon autoclave: 48 parts deionized $H_2O$, 1 part $Al_2(SO_4)_3$ (17% $Al_2O_3$), 5 parts KOH (45% solution), 8.18 parts Ultrasil TM VN3 precipitated silica (North American Silica Company), 3.63 parts ethylpyridinium bromide (SWAC, 50% aqueous solution,), and 0.5 part ZSM-22 seeds (similarly prepared but on a smaller scale with colloidal silica (Q-Brand) as the silicon source). The mixture was aged with stirring at 93° C. for 16 hours at 90 rpm, then crystallized at 160° C. while stirring at 180 rpm for 78 hours. The composition of the reactant gel is described in molar quantities as follows:

| | |
|---|---|
| $SiO_2/Al_2O_3$ | 73 |
| $OH^-/SiO_2$ | 0.23 |
| $N/SiO_2$ | 0.07 |
| $H_2O/SiO_2$ | 23 |
| $N/Al_2O_3$ | 5.4 |
| $OH^-/H_2O$ | 0.01 |

The product was water washed, then calcined at 540° C., first in $N_2$ for three hours, then full air for another 6 hours, to decompose the organic directing agent. The calcined product was exchanged with $NH_4NO_3$ four times to remove the potassium. After complete exchange, the product was dried again in air for 3 hours to decompose the $NH_4$ leaving the acid form of the zeolite. Product properties are as follows:

| | |
|---|---|
| $SiO_2/Al_2O_3$ | 73 |
| BET Surface Area | 230 $m^2/g$ |
| Static adsorption: | |
| $H_2O$ | 6.6 wt % |
| n-hexane | 7.7 wt % |
| cyclohexane | 4.4 wt % |

Scanning electron microscopy (SEM) and transmission electron microscopy (TEM) (see FIG. 1), on a sample from a different batch made by the same procedure of this Example, indicated that the largest dimension of the product crystals was less than 0.5 micron. The product exhibited the characteristic X-ray diffraction pattern of ZSM-22.

The zeolite was then blended 65 parts zeolite and 35 parts Ultrasil ™ VN3 and pelleted. The pellets were sized 14/24 mesh and recalcined at 538° C. in flowing air for 3 hours.

EXAMPLE 2

Preparation of Theta-1 (TON-C) (Comparative)

Sodium aluminate (41% w/w $Al_2O_3$, 29.6% w/w $Na_2O$, 29.4% w/w $H_2O$ (2.09 parts) and sodium hydroxide (1.00 part) were dissolved in distilled water (20.9 parts). Diethanolamine (DEA, 26.9 parts) was added and the mixture thoroughly stirred. Distilled water (52.9 parts) was added with stirring, followed by addition of colloidal silica (74.3 parts) (DuPont Ludox AS40 40% w/w $SiO_2$) to the mixture which was then well stirred to give a homogeneous gel. The gel was charged to a stainless steel autoclave and crystallized for 28 hours at 175° C. with stirring after which the product was filtered, washed well with distilled water and dried in an oven at 120° C.

Figure 2:
FIG. 2 is a transmission electron microscopy (TEM) micrograph of the large crystal Theta-1 sample of Example 2.

The product was next refluxed with aqueous ammonium nitrate solution (10 g/200 ml) (1M. 2×1 hr.), filtered hot, washed well with distilled water, dried in an oven at 120° C. and calcined at 325° C. in air for 8 hours. The zeolite was blended 65 parts zeolite and 35 part Ultrasil ™ VN3 and pelleted. The pellets were sized 14/24 mesh and recalcined at 325° C. in flowing air for 3 hours, packed into a silica reactor and activated overnight in air at 350° C. in situ. The system was flushed through with nitrogen and the temperature was increased to 400° C. under nitrogen. Scanning electron microscopy and transmission electron microscopy indicate the Theta-1 crystals have acicular lathe (needle-like) morphology with a broad distribution of crystal sizes having the largest dimension of up to 1 to 2 microns. FIG. 2 is a TEM micrograph of the Theta-1 thus prepared.

This catalyst was prepared in accordance with the procedure set out in European patent application 0 247 802 for the material designated TON-C. The resulting product was used to duplicate two runs set out in Table 7 therein, the first with pure 1-butene feed at 13 WHSV (at 100 kPa) and the second with 10% 1-butene, 90% nitrogen at 4.7 WHSV. A comparison of the results under the first set of conditions is presented below:

| | Example 2 Catalyst | TON-C |
|---|---|---|
| NC4 = Conv. (%) | 58.2 | 53.0 |
| IC4 = Yield (%) | 25.8 | 25.5 |
| IC4 = Sel. (%) | 44.3 | 48.1 |

A comparison of the results under the second set of conditions is also set out below:

| | Example 2 Catalyst | TON-C |
|---|---|---|
| NC4 = Conv. (%) | 29.4 | 30.6 |
| IC4 = Yield (%) | 27.0 | 27.9 |
| IC4 = Sel. (%) | 91.6 | 91.2 |

The foregoing results show that the catalyst prepared in Example 2 duplicates the performance of the TON-C catalyst.

EXAMPLE 3

Isomerization of 1-Butene with Microcrystalline ZSM-22 and Theta-1 at 550° C.

The microcrystalline ZSM-22 of Example 1 and Theta-1 of Example 2 were used in butene skeletal isomerization reactions carried out at 400° C. and 550° C., and at 75 WHSV and 21 WHSV. Further process conditions and results are provided below:

| | Run No. | | | |
|---|---|---|---|---|
| | 1 | 2 | 3 | 4 |
| WHSV (HC) | 75 | 75 | 21 | 21 |
| T (°C.) | 400 | 550 | 400 | 550 |
| P (kPa) | 160 | 160 | 160 | 160 |
| $N_2/1$-C4 = (v/v) | 3 | 3 | 10 | 10 |
| Microcrystalline ZSM-22 | | | | |
| Conv. (%) | 44.3 | 40.6 | 40.4 | 39.8 |
| IC4 = Yld (%) | 27.1 | 35.8 | 33.6 | 37.6 |
| IC4 = Sel (%) | 61.1 | 88.1 | 83.3 | 94.5 |
| Theta-1 | | | | |
| Conv. (%) | 3.6 | 34.9 | 26.6 | 35.2 |
| IC4 = Yld (%) | 3.2 | 33.0 | 24.1 | 33.3 |
| IC4 = Sel (%) | 87.7 | 94.5 | 90.5 | 94.5 |

The results indicate that the microcrystalline ZSM-22 catalyst has significantly higher activity than the large crystal Theta-1 catalyst, particularly at lower temperatures (400° C.) and higher WHSV. Moreover, total iso-olefin yield is consistently higher with microcrystalline ZSM-22 despite somewhat reduced selectivity at lower temperature and lower WHSV.

It is claimed:

1. A method for conversion of linear olefins to corresponding iso-olefins of the same carbon number which comprises contacting a linear olefin-containing organic feedstock with a catalyst comprising material having the structure of ZSM-22 having a crystal size whose largest dimension is no greater than 0.5 micron, and whose ratio of its second largest dimension to said largest dimension ranges from 0.5 to 1, under skeletal isomerization conditions, wherein said conversion is carried out at temperatures between about 250° and 750° C., weight hourly space velocities (WHSV) based on linear olefins in said feedstock between 1 and 500 WHSV, linear olefin partial pressures between 12 and 500 kPa, and conversion levels of at least 20 weight percent.

2. The method of claim 1 wherein said temperatures are between about 325° and 600° C., said weight hourly space velocities (WHSV) are between 5 and 400, said linear olefin partial pressure is between 30 and 300 kPa, and conversion levels of at least 30 weight percent.

3. The method of claim 1 wherein said temperatures are between about 390° and 550° C., said weight hourly space velocities (WHSV) are between 10 and 250, said linear olefin partial pressure is between 50 and 150 kPa, and conversion levels of at least 35 weight percent.

4. The method of claim 1 wherein said temperatures are no greater than 450° C.

5. The method of claim 4 wherein said WHSV is no less than 5.

6. The method of claim 1 wherein said largest dimension of said crystal size is less than 0.3 micron.

7. The method of claim 1 wherein said crystal size has the dimensions of 0.2 to 0.4 micron by 0.1 to 0.4 micron by ≦0.1 micron.

8. The method of claim 1 wherein said feedstock comprises $C_4$ to $C_{10}$ linear olefins.

9. The method of claim 1 wherein said feedstock comprises $C_4$ to $C_6$ linear olefins.

10. The method of claim 1 wherein said catalyst is reactivated by exposure to hydrogen at temperatures of at least 400° C. for a time sufficient to effect reactivation.

11. The method of claim 1 wherein said catalyst is reactivated by exposure to oxygen at temperatures of at least 350° C. for a time sufficient to effect reactivation.

12. The method of claim 1 wherein said catalyst comprises 10 to 99 wt % of a refractory inorganic oxide binder.

13. The method of claim 1 wherein said catalyst comprises 20 to 70 wt % of a silica binder.

14. The method of claim 1 wherein said organic feedstock comprises at least 5 wt % n-butenes.

15. The method of claim 1 wherein said organic feedstock consists essentially of a $C_4$ hydrocarbon stream.

16. The method of claim 1 wherein said organic feedstock consists essentially of a $C_{4+}$ hydrocarbon stream.

17. The method of claim 1 wherein said conversion results in less than 5% conversion to products of lower or higher average carbon number.

18. A method for conversion of linear olefins to corresponding iso-olefins of the same carbon number which comprises contacting a linear olefin-containing organic feedstock with a catalyst comprising materials having the structure of ZSM-22 prepared from a forming mixture comprising ethylpyridinium, under skeletal isomerization conditions, wherein said conversion is carried out at temperatures between about 250° and 750° C., weight hourly space velocities (WHSV) based on linear olefins in said feedstock between 1 and 500 WHSV, linear olefin partial pressures between 12 and 500 kPa, and conversion levels of at least 20 weight percent.

* * * * *